(12) United States Patent
Rogan

(10) Patent No.: US 11,357,259 B2
(45) Date of Patent: Jun. 14, 2022

(54) RESERVOIR ASSEMBLY FOR A PERSONAL VAPORIZER DEVICE

(71) Applicant: JT International S.A., Geneva (CH)

(72) Inventor: Andrew Robert John Rogan, Forres (GB)

(73) Assignee: JT International S.A.

( * ) Notice: Subject to any disclaimer, the term of this patent is extended or adjusted under 35 U.S.C. 154(b) by 871 days.

(21) Appl. No.: 15/781,029

(22) PCT Filed: Dec. 2, 2016

(86) PCT No.: PCT/EP2016/079528
§ 371 (c)(1),
(2) Date: Jun. 1, 2018

(87) PCT Pub. No.: WO2017/093452
PCT Pub. Date: Jun. 8, 2017

(65) Prior Publication Data
US 2020/0146351 A1    May 14, 2020

(30) Foreign Application Priority Data
Dec. 3, 2015    (EP) .................................... 15197778

(51) Int. Cl.
*A24F 40/42*    (2020.01)
*A24F 40/485*    (2020.01)
*A24F 40/10*    (2020.01)

(52) U.S. Cl.
CPC ............ *A24F 40/42* (2020.01); *A24F 40/485* (2020.01); *A24F 40/10* (2020.01)

(58) Field of Classification Search
None
See application file for complete search history.

(56) References Cited

U.S. PATENT DOCUMENTS 4,171,000 A * 10/1979 Uhle ..................... A61M 15/06
131/273
5,623,920 A    4/1997 Bryant
(Continued)

FOREIGN PATENT DOCUMENTS

| FR | 2497913 A2 | 7/1982 |
| GB | 2076899 A | 12/1981 |
| WO | 2015027436 A1 | 3/2015 |

OTHER PUBLICATIONS

Extended European Search Report for EP Application No. 15197778. 2, dated Aug. 16, 2016.
(Continued)

*Primary Examiner* — Michael J Felton
(74) *Attorney, Agent, or Firm* — Lerner, David, Littenberg, Krumholz & Mentlik, LLP

(57) ABSTRACT

A reservoir assembly is provided for a personal vaporizer device, such as an electronic smoking article or an e-cigarette. The reservoir assembly comprises a housing which encloses a reservoir for storing a liquid to be vaporized, wherein the housing and/or the reservoir define a flow path for the liquid from the reservoir for vaporization of the liquid. The reservoir assembly further comprises a mouthpiece provided in or on the housing and defining a channel for conveying vapour formed from the liquid to a user's mouth. The mouthpiece is configured for movement between a first position and a second position, wherein the flow path is closed or blocked when the mouthpiece is in the first position and wherein the flow path is open in the second position. Also provided is a personal vaporizer device, such as an electronic smoking article or an e-cigarette, which includes such a reservoir assembly.

13 Claims, 5 Drawing Sheets

(56) References Cited

U.S. PATENT DOCUMENTS

2008/0265198 A1 10/2008 Warby
2011/0290244 A1 12/2011 Schennum
2015/0173417 A1 6/2015 Gennrich et al.

OTHER PUBLICATIONS

International Search Report for PCT Application No. EP 2016079528, dated Mar. 2, 2017.

* cited by examiner

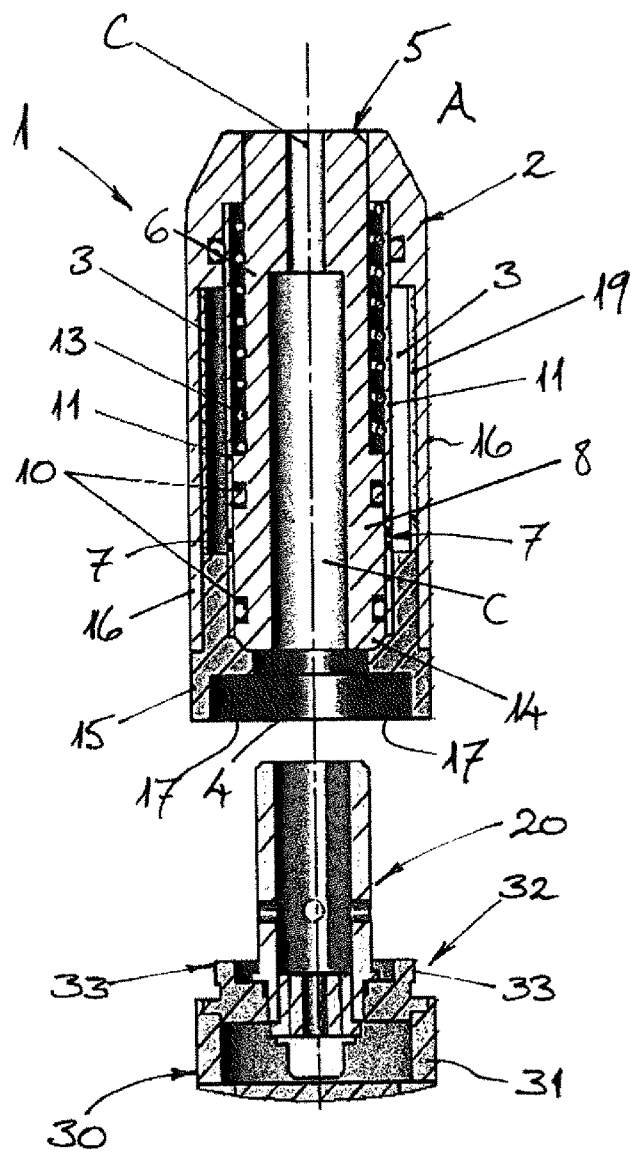
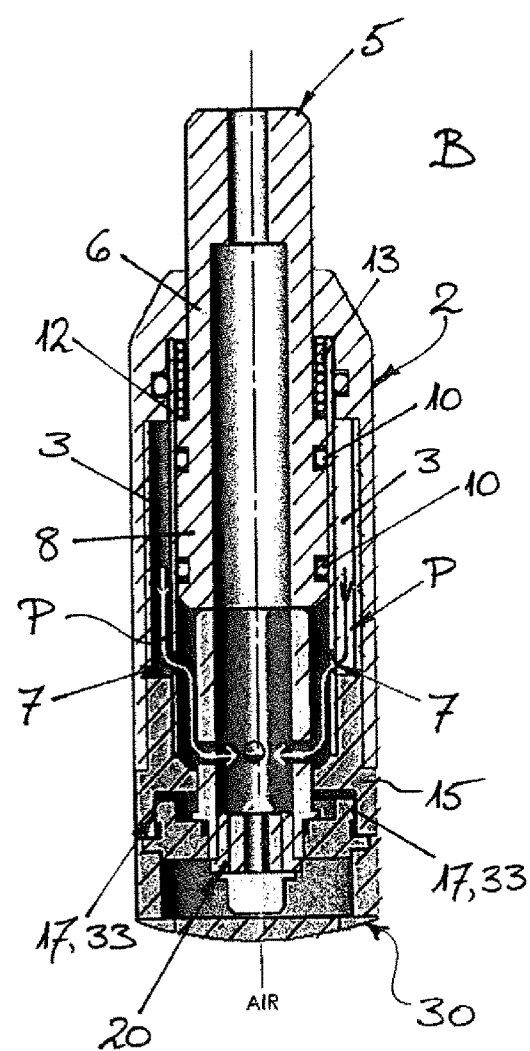
Fig. 3
Fig. 4

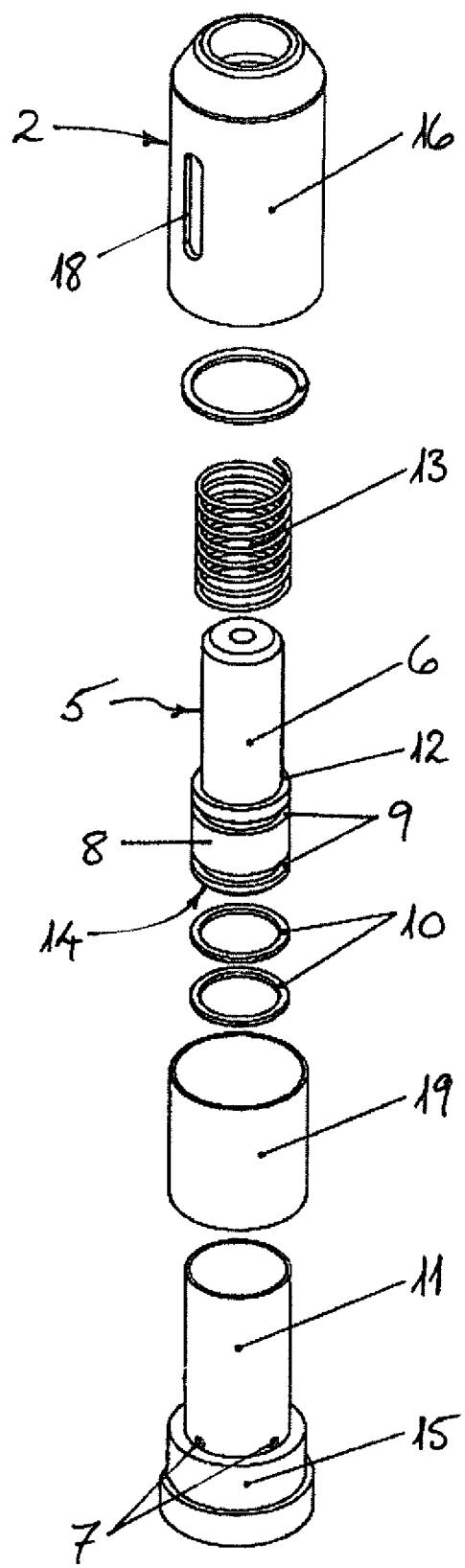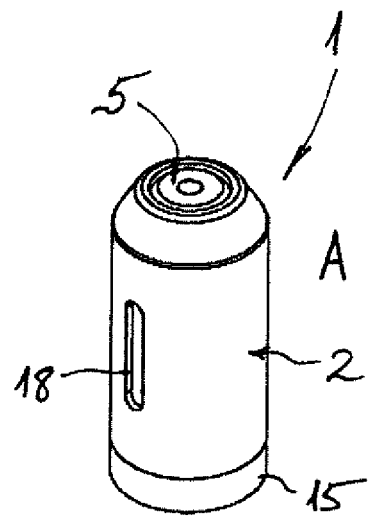
Fig. 5a
Fig. 5b

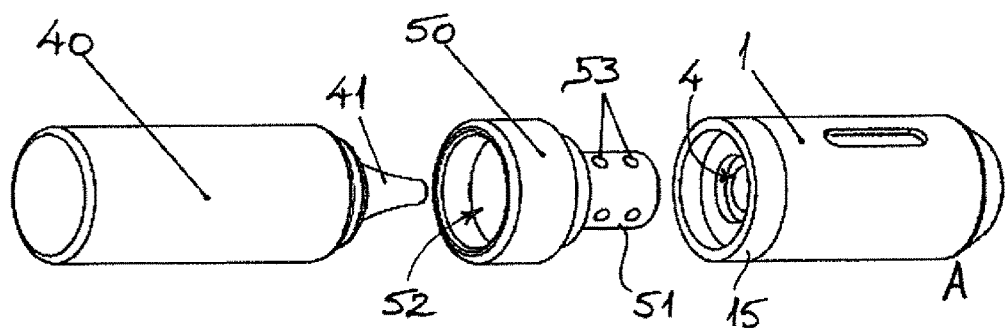
Fig. 6
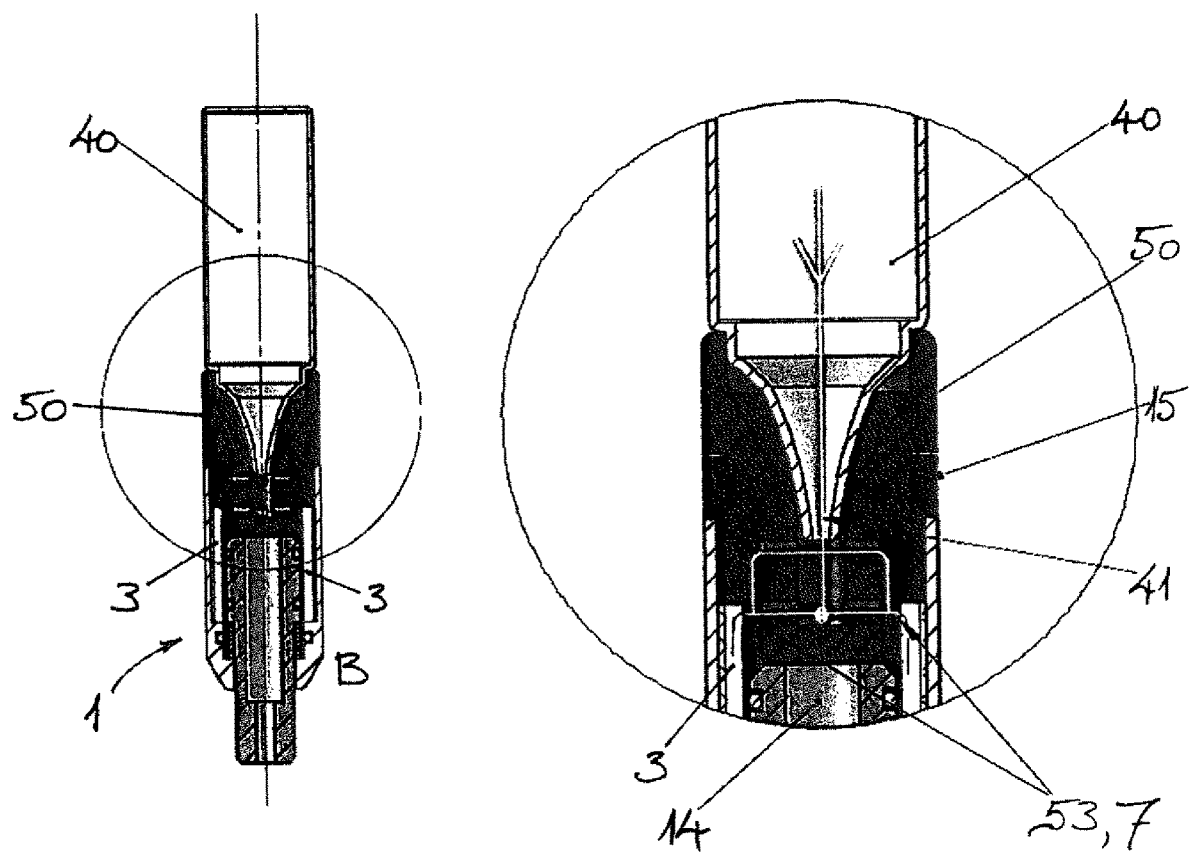
Fig. 7
Fig. 8

RESERVOIR ASSEMBLY FOR A PERSONAL VAPORIZER DEVICE

CROSS-REFERENCE TO RELATED APPLICATIONS

The present application is a national phase entry under 35 U.S.C. § 371 of International Application No. PCT/EP2016/079528, filed Dec. 2, 2016, published in English, which claims priority to European Application No. 15197778.2 filed Dec. 3, 2015, the disclosures of which are incorporated herein by reference.

FIELD OF THE INVENTION

The present invention relates to a reservoir assembly for an inhaler device, such as a personal vaporizer device, an electronic smoking article or e-cigarette. This invention is thus particularly applicable to cartridges, especially refillable e-liquid units and replaceable e-liquid units, for electronic smoking articles or e-cigarettes. The invention naturally also relates to an inhaler device which includes such a reservoir assembly.

BACKGROUND OF THE INVENTION

Personal vaporizer devices, such as electronic cigarettes or "e-cigarettes" as they are also known, have gained in popularity over the past ten years as an alternative to traditional smoking articles, like cigarettes, cigars, and cigarillos. Because the technology employed in personal vaporizer devices is still quite young, however, developments in the design and configuration of such devices are on-going to improve their performance and their reliability, as well as their ease of production and their production costs.

SUMMARY OF THE INVENTION

In view of the above, an object of the invention is to provide a new and improved reservoir assembly for an inhaler device, such as a personal vaporizer device or electronic smoking article or e-cigarette. It would be especially desirable to provide such a reservoir assembly which remains sealed and prevents leakage before it is deployed for use. It would be desirable to provide such a reservoir assembly which is able to be unsealed and deployed for use in a simple and convenient manner.

Furthermore, it would be useful to provide a reservoir assembly which substantially inhibits a user from accessing the liquid held in the reservoir assembly without an appropriately designed tool or adapter.

In accordance with the present invention, a reservoir assembly for an inhaler device, such as a personal vaporizer device, an electronic smoking article or e-cigarette, is provided as recited in claim 1. Various advantageous and/or preferred features of the invention are recited in the dependent claims.

According to one aspect, therefore, the present invention provides a reservoir assembly for a personal vaporizer device, such as an electronic smoking article, comprising:
  a housing which encloses a reservoir for storing a liquid to be vaporized, the housing and/or the reservoir defining a flow path for the liquid from the reservoir or out of the reservoir for vaporization;
  a mouthpiece provided in or on the housing and defining a channel for conveying vapour formed from the liquid to a user's mouth;
  wherein the mouthpiece is configured for movement between a first, non-use position and a second, use position, wherein the flow path is closed or blocked when the mouthpiece is in the first position and wherein the flow path is open in the second position.

In this way, the reservoir assembly of the invention is configured to close, block or seal the liquid flow path to prevent leakage of liquid from the reservoir in the first, non-use position. Where the reservoir assembly is embodied as a cartridge or a replaceable or refillable e-liquid unit for an electronic smoking article or e-cigarette, therefore, the cartridge or the replaceable or refillable e-liquid unit may be held and stored prior to use with the mouthpiece in the first (non-use) position to prevent or avoid any unwanted leakage of the liquid from the reservoir. Indeed, the reservoir assembly is desirably configured such that a user has no access to the liquid stored or held in the reservoir without an appropriate tool or adapter to move the mouthpiece from the first, non-use position to the second position. This may act to inhibit a user from inadvertently coming in contact with the liquid and/or from re-filling the reservoir with inappropriate liquid. The configuration of the invention thus provides a valve mechanism in the reservoir assembly.

In a preferred embodiment, a part of the mouthpiece itself is configured to close or block the flow path in the first position. That is, the mouthpiece, or a part thereof, may form a valve member or valve body for closing or sealing the flow path. For example, the flow path may comprise a port formed in a wall of the reservoir. The mouthpiece preferably comprises a sealing portion which is configured to cover or block the port when the mouth-piece is in the first position. To this end, the sealing portion of the mouthpiece may include one or more seal member, such as an O-ring, for closing or sealing the flow path (e.g. at the flow port formed in a wall of the reservoir) against fluid flow. In one specific example, the sealing portion of the mouthpiece may include two seal members, such as O-rings, spaced apart from one another and the port may be located between those seal members in the first (non-use) position.

In a preferred embodiment, in the first position the mouthpiece is configured to be substantially retracted into the housing. By way of contrast, in the second position the mouthpiece is preferably configured to extend or project from the housing.

In a preferred embodiment, the mouthpiece comprises an elongate member with the channel extending longitudinally, and preferably substantially centrally, thereof. Thus, the mouthpiece may be movable in the longitudinal direction between the first position and the second position.

In a preferred embodiment, the mouthpiece of the reservoir assembly is resiliently biased, especially by spring means, towards the first position. In this way, the reservoir assembly is configured such that the "normal" position of the mouthpiece is the first (i.e. non-use) position when the reservoir assembly is in isolation; e.g. when the reservoir assembly is not yet installed or deployed in an e-cigarette.

In a preferred embodiment, the mouthpiece is configured for translational or sliding movement between the first position and the second position, e.g. along a central or longitudinal axis of the mouthpiece and/or of the housing. Alternatively and/or in addition, the mouthpiece may be configured for rotational movement between the first position and the second position.

In a preferred embodiment, the housing is configured to receive, at least partially, an aerosol generating unit of the personal vaporizer device. The mouthpiece may thus be configured for movement from the first position to the second position when the aerosol generating unit is inserted into or received in the housing. The mouthpiece may then be configured for movement from the second position to the first position when the aerosol generating unit is removed or withdrawn from the housing. In this regard, insertion of the aerosol generating unit into the housing of the reservoir assembly typically takes place when the reservoir assembly is being connected with or mounted on the personal vaporizer device. In other words, when a new reservoir assembly (e.g. in the form of a cartridge) is being attached to or assembled with the personal vaporizer device or e-cigarette, the housing may at least partially receive the aerosol generating unit, which in turn acts upon the mouthpiece to move it from the first, non-use position to the second, use position, optionally against a spring bias. In this way, the aerosol generating unit may form or act as a tool for moving the mouthpiece and accessing the liquid stored or held in the reservoir. Similarly, if the reservoir is depleted of liquid, or the user simply wishes change to a different cartridge (e.g. with a different liquid), the disassembly of the personal vaporizer device or e-cigarette to demount or detach the cartridge may typically involve removal of the aerosol generating unit from within the housing. This may then enable the mouthpiece to move back from the second, use position to the first, non-use position, e.g. under the spring bias. This again seals or closes the liquid flow path to inhibit a user from inadvertently coming in contact with the liquid remaining in the reservoir.

According to another aspect, the present invention provides a reservoir assembly for an inhaler device, such as a personal vaporizer device or electronic smoking article, comprising:

a housing which encloses a reservoir for storing a liquid to be vaporized, the housing and/or the reservoir defining a flow path for the liquid from the reservoir for vaporization; and valve means provided in the housing for movement between closed position preventing liquid flow from the reservoir along the flow path and an open position permitting liquid flow from the reservoir along the flow path.

In a preferred embodiment, the reservoir assembly includes a mouthpiece which is provided in the housing and defines a channel for conveying vapour formed from the liquid to a user's mouth. The mouthpiece is configured for movement between a first position and a second position, wherein the first position of the mouthpiece corresponds to the closed position of the valve means and wherein the second position of the mouthpiece corresponds to the open position of the valve means. In this regard, the valve means may be provided on, or formed by, the mouthpiece such that movement of the mouthpiece between the first and second positions effects movement of the valve means between the open and closed positions of the flow path.

In a preferred embodiment, the reservoir assembly of the invention is configured to cooperate with a refill bottle, wherein the housing is configured to receive, at least partially, a neck or a nozzle of the refill bottle. In this regard, insertion of the neck or nozzle of the refill bottle into the housing is adapted to effect movement of the valve means from the closed to the open position—i.e. movement of the mouth-piece from the first position to the second position. This thereby opens the flow path to enable refill liquid to flow from the neck or nozzle of the bottle (e.g. under pressure created by manually squeezing the flexible refill bottle) into the reservoir.

In one preferred embodiment, the neck or nozzle of the refill bottle is configured to fit within the housing and to cooperate with the mouthpiece directly to move the mouthpiece from the first to the second position. In an alternative embodiment, a refill adapter is provided for insertion into the housing between the refill bottle and the reservoir assembly of the invention. In this way, by designing a neck or nozzle of the refill bottle to fit within the housing and to cooperate with the mouthpiece directly as an adapter, or by providing a separate adapter member, the cartridge or reservoir assembly of the invention is configured to inhibit a user from re-filling the reservoir with an inappropriate or incompatible liquid. Furthermore, the design acts to inhibit a user from inadvertently coming into direct contact with the liquid.

According to another aspect, the present invention provides a personal vaporizer device, especially an electronic smoking article or e-cigarette, which comprises: a reservoir assembly according to any one of the aspects or embodiments described above; an aerosol generating means for vaporizing the liquid from the reservoir; and a power supply for powering the aerosol generating means to vaporize the liquid from the reservoir.

In a preferred embodiment, the housing is configured to receive, at least partially, the aerosol generating means of the personal vaporizer device. The mouthpiece is preferably configured for movement from the first position to the second position upon insertion of the aerosol generating means into the housing.

In a preferred embodiment, the power supply comprises a casing configured for connection with and/or for supporting the housing of the reservoir assembly. The power supply preferably comprises a battery unit and the casing is configured for a friction fit or, alternatively, for a threaded or a latched connection with the reservoir assembly housing.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which:

FIG. 3 is a cross-sectional view of the reservoir assembly shown in FIG. 1 in the first position prior to mounting it on or connection it with a base of the electronic cigarette;

FIG. 4 is a cross-sectional view of the reservoir assembly as shown in FIG. 1 in the second position after mounting it on or connection it with the base of the electronic cigarette;

FIG. 5a is an exploded view of the reservoir assembly shown in FIG. 1;

FIG. 5b is a perspective view of the reservoir assembly shown in FIG. 1 in the first position prior to mounting it on or connection it with a base of the electronic cigarette;

FIG. 6 is a perspective view of the reservoir assembly of FIG. 1 with a refill adapter and a refill bottle for refilling the reservoir;

FIG. 7 is a cross-sectional view of the reservoir assembly combined with the refill adapter and the refill bottle of FIG. 6 for refilling the reservoir;

FIG. 8 is a detailed cross-sectional view of the reservoir assembly combined with the refill adapter and the refill bottle from FIG. 7;

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will further be appreciated that certain actions and/or steps in an embodiment of a method may be described or depicted in a particular order of occurrences while those skilled in the art will understand that such specificity with respect to sequence is not actually required. It will also be understood that the terms and expressions used in the present specification have the ordinary meaning as is accorded to such terms and expressions with respect to their corresponding respective areas of inquiry and study, except where specific meanings have otherwise been set forth herein.

DETAILED DESCRIPTION OF EMBODIMENTS

Figures 1, 2:
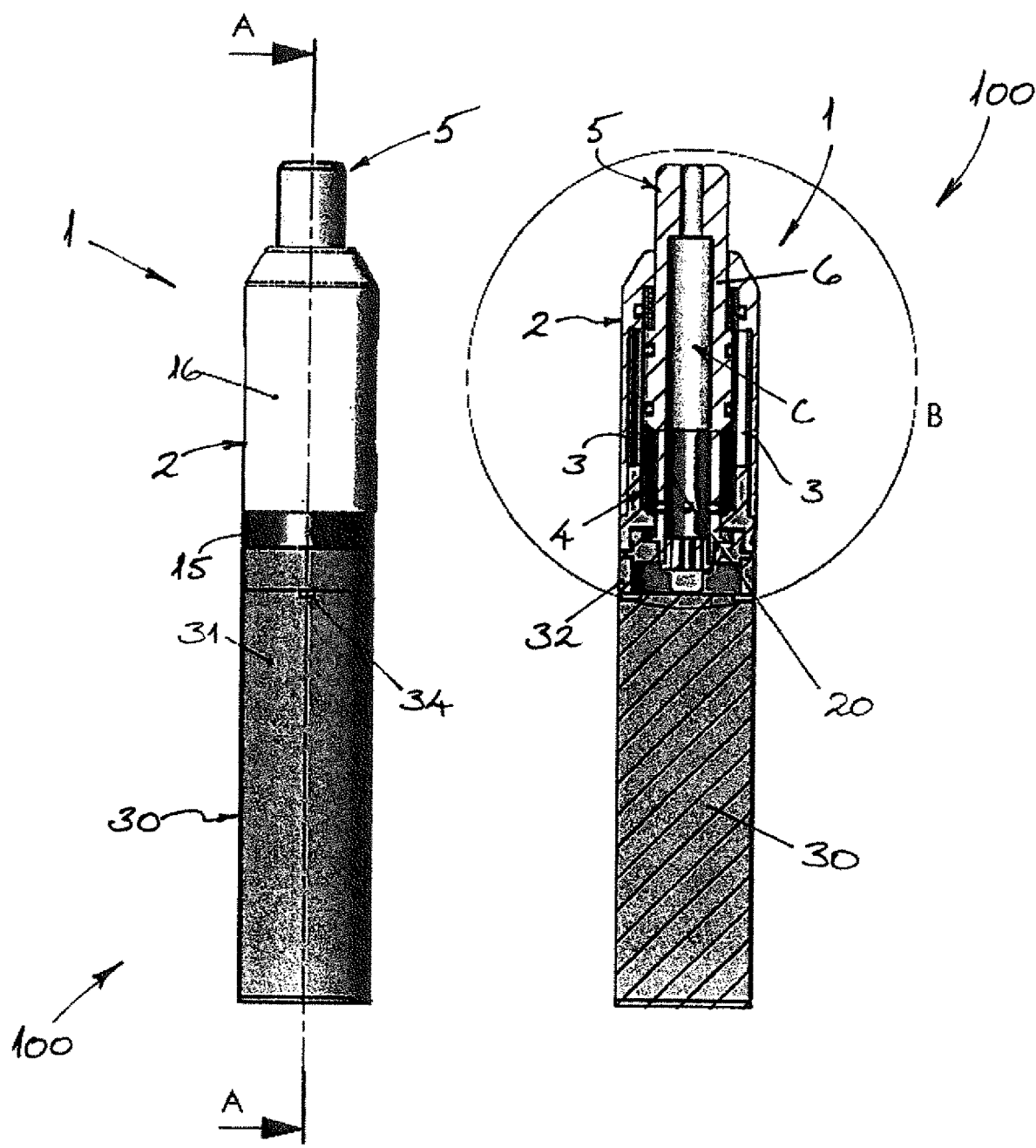
FIG. 1 is a schematic front view of an electronic cigarette having a reservoir assembly according to a preferred embodiment of the invention.
FIG. 2 is a cross-sectional view of the electronic cigarette shown in FIG. 1 taken in the direction of arrows A-A.

With reference firstly to FIGS. 1 and 2 of the drawings, an inhaler device 100 in the form of a personal vaporizer device (also known as an electronic smoking article or an "e-cigarette") according to a preferred embodiment is illustrated.

The personal vaporizer device or e-cigarette 100 is generally elongate and has a substantially circular cylindrical shape. The e-cigarette 100 comprises a reservoir assembly 1 according to a preferred embodiment, which is provided in the form of a refillable cartridge. The reservoir assembly or cartridge 1 comprises a housing 2 which encloses a reservoir 3 for storing a liquid to be vaporized. The reservoir 3 has a generally annular form and surrounds a central cavity or chamber 4 in the housing 2 which accommodates a mouthpiece 5. The mouthpiece 5 comprises an elongate member 6 and has a longitudinally extending channel C for conveying vapour formed from the liquid to a mouth of a person using the e-cigarette 100. The reservoir assembly or cartridge 1 is mounted on a power supply unit 30 which stores electrical potential or energy, e.g. in one or more batteries, enclosed within a cylindrical casing 31 of that unit 30. The power supply unit 30 is provided for delivering electrical power to an aerosol generating unit 20 connected at an end region 32 of the casing 31. The aerosol generating unit 20 extends or projects at least partially into the housing 2 of the reservoir assembly or cartridge 1 and is configured to receive liquid from the reservoir 3 to be vaporized. For this reason, the aerosol generating unit 20 also communicates fluidly with the channel C in the mouthpiece 5 for delivering the vapour generated to the user.

With reference also now to FIGS. 3, 4, 5*a* and 5*b* of the drawings, the construction of the reservoir assembly or cartridge 1 is illustrated in greater detail. Comparing the views of the cartridge 1 in FIGS. 3 and 5*b* with the views in FIGS. 1, 2 and 4, it will be noted that the mouthpiece 5 of the cartridge 1 is configured for movement between a first, retracted position A (i.e. as seen in FIGS. 3 and 5*b*) and a second, extended position B (i.e. as seen in FIGS. 1, 2 and 4). In this regard, FIG. 4 shows a cross-sectional detail of the second position B seen in FIG. 2. The operation and purpose or function of this movable mouthpiece member 6 is explained below.

As is clear from FIG. 4, the reservoir assembly or cartridge 1 defines a flow path P for the liquid from the reservoir 3 to travel to the aerosol generating unit 20 where it is then vaporized. The flow path P includes one or more outlet port 7 formed in a wall of the reservoir 3, through which the liquid may flow under gravity and/or via capillary action (e.g. in the event of a narrow channel being provided) along the path P in the direction of the arrows towards the aerosol generating unit 20. As is particularly apparent from FIGS. 3, 4 and 5*a*, the elongate mouthpiece member 6 includes a valve part or sealing part 8 having two circumferential grooves or slots 9 axially spaced apart and each accommodating a sealing element 10, such as a flexible O-ring. The valve part or sealing part 8 of mouthpiece member 6 has an outer diameter only marginally smaller than an inner diameter of the central cavity or chamber 4 in the housing 2, such that the O-rings 10 engage and seal against an inner wall 11 of the cavity or chamber 4. It is to be appreciated that this inner wall 11 of the central cavity 4 also constitutes the wall of the reservoir 3 in which the outlet ports 7 are formed.

An end of the valve part or sealing part 8 of the mouthpiece 5 directed towards the user presents an annular shoulder 12 against which a coil spring 13 bears to bias the mouthpiece 5 to the first, retracted position A shown in FIG. 3. The valve part or sealing part 8 of mouthpiece member 6 is configured and dimensioned such that, in this first position A, the flow path P is closed or blocked by the valve or sealing part 8 of the mouthpiece 5. This occurs because, in the first position A, the outlet ports 7 of the reservoir 3 are located between the O-rings 10, which seal against the wall 11 of the cavity or chamber 4 and prevent any flow of the liquid from the reservoir 3 to aerosol generating unit 20. This first position A therefore forms or represents a non-use position in which the reservoir assembly or cartridge 1 is disabled and the valve part or valve means 8 effectively seals or closes the flow path P against leakage of liquid from the reservoir 3. Further, in the first position A, a base 14 of the valve part 8 (i.e. mouthpiece member 6) seats against a retaining collar 15, which is connected (e.g. in a press-fit or in a threaded connection) with the cartridge housing 2 (e.g. an outer shell 16 of the housing) to retain the mouth-piece member 6 in the central cavity 4. The retaining collar 15 will typically also include one or more connector elements 17, such as a clip or a screw thread, at a side thereof facing the power supply unit 30 for engagement with complementary connector elements 33 at the end region 32 of the casing 31.

The various components of the reservoir assembly or cartridge 1 described above are illustrated in the exploded view shown in FIG. 5*a*. As can be seen, the outer shell 16 of the cartridge housing 2 includes a window cut-out 18 and a transparent liner 19 is inserted therein to line the inside of the outer shell 16 and form an outer wall of the reservoir 3. Because the liner 19 is transparent, a user is able to see through the window 18 how much liquid remains in the reservoir 3 at any given time.

Referring again to FIGS. 3 and 4 of the drawings, when the reservoir assembly or cartridge 1 is mounted to the end region 32 of the power supply casing 31 at which the aerosol generating unit 20 is electrically and physically connected, the aerosol generating unit 30 extends or projects partially into the cartridge housing 2. More particularly, an end portion of the aerosol generating unit 30 engages the base 14 of the mouthpiece member 6 and, as it is inserted into the housing cavity 4, moves the mouthpiece member 6 relative to the housing 2 from the first position A shown in FIG. 3 to the second position B shown in FIG. 4. That is, the mouthpiece 5 moves against the bias of the compression spring 13 to the position B in which it projects from the housing 2 for ready access by a user to draw upon it and inhale vapour from the channel C. In moving to the second position B, the valve part 8 of the mouthpiece member 6 moves out of the previous sealing or blocking position seen in FIG. 3 to open the flow path P permitting liquid from the reservoir 3 to flow to the aerosol generating unit 30, as seen in FIG. 4.

With reference now to drawing FIGS. 6 to 8, an example is illustrated of how the reservoir assembly or refillable cartridge 1 of the invention may be configured to cooperate with a refill bottle 40. In this example, a refill adapter 50 is provided for insertion into the cavity 4 of the housing 2 between the refill bottle 40 and the cartridge 1. The adapter 50 includes a projecting nose member 51 configured to fit the cavity 4 and to engage with the base 14 of the mouthpiece member 6 to move it into the second position B against the bias of the spring 13. This opens the flow path P to the reservoir 3 via the flow ports 7. Because the cartridge 1 is held inverted, any liquid remaining in the reservoir 3 is unable to flow out of the ports 7. A nozzle 41 of the refill bottle 40 is inserted into a complementary tapered hollow or recess 52 provided at a side of the adapter 50 opposite the nose member 51. By manually squeezing the flexible refill bottle 40, the refill liquid in the bottle is forced out of the nozzle 41 and into the reservoir 3 via dispensing openings 53 in nose member 51 and via the ports 7.

Figure 9:
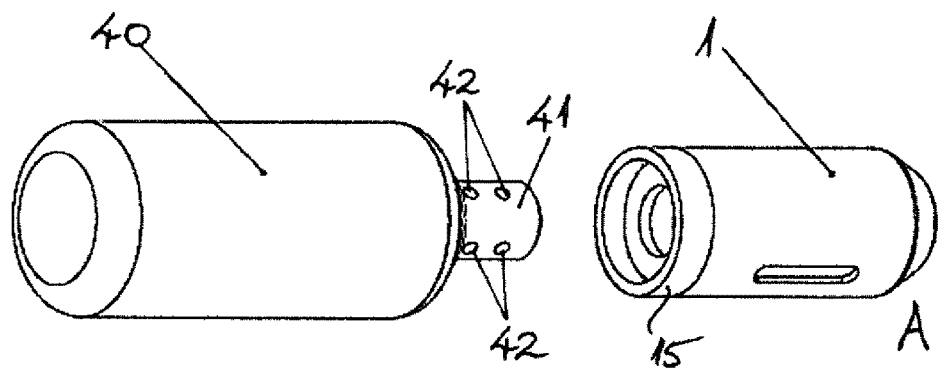
FIG. 9 is a perspective view of the reservoir assembly of FIG. 1 with a refill bottle for refilling the reservoir.
Figures 10, 11:
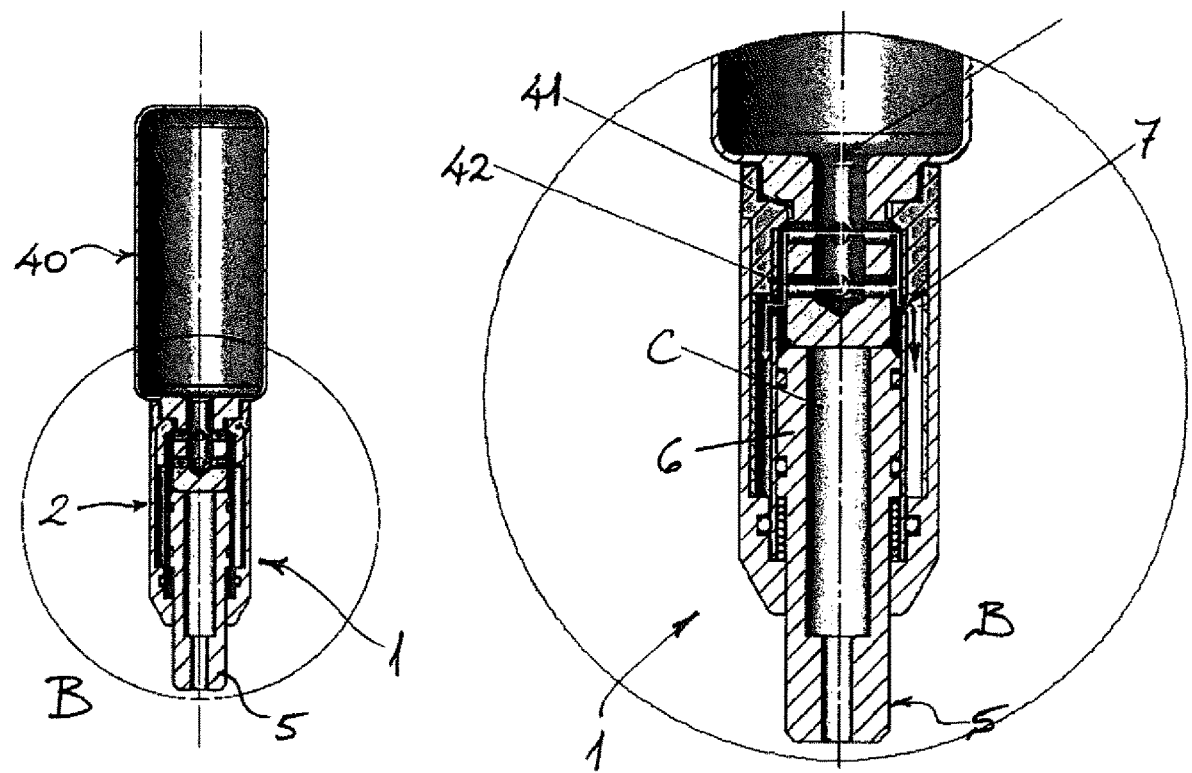
FIG. 10 is a cross-sectional view of the reservoir assembly combined with the refill bottle of FIG. 9 for refilling the reservoir.
FIG. 11 is a detailed cross-sectional view of the reservoir assembly combined with the refill bottle from FIG. 10.

Referring to drawing FIGS. 9 to 11, an alternative example is provided of how the reservoir assembly or refillable cartridge 1 of the invention may be configured to cooperate with a refill bottle 40. In this example no adapter 50 is required because the nozzle or neck 41 of the bottle 40 is already configured to fit the cavity 4 and to engage with the base 14 of the mouthpiece member 6 to move it into the second position B against the bias of the spring 13. Furthermore, the nozzle or neck 41 of the bottle 40 is provided with a plurality of radially directed dispensing openings 42 for delivery of the refill liquid to the reservoir via the ports 7, as described above.

Although specific embodiments of the invention are illustrated and described herein, it will be appreciated by those of ordinary skill in the art that a variety of alternate and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

LIST OF DRAWING SIGNS 1 reservoir assembly
2 housing
3 reservoir
4 central cavity or chamber
5 mouthpiece
6 mouthpiece member
7 outlet port
8 valve part or sealing part
9 groove or slot
10 sealing element or O-ring
11 wall of cavity and of reservoir
12 annular shoulder
13 compression spring
14 base of valve part or mouthpiece member
15 retaining collar
16 outer shell of the housing
17 connector element
18 window
19 liner
20 aerosol generating unit
30 power supply unit or battery unit
31 casing
32 end region of casing
33 connector element
34 air inlet in casing
40 refill bottle
41 nozzle or neck
42 dispensing opening
50 adapter member
51 nose member
52 hollow or recess
53 dispensing opening
100 vaporizer device or e-cigarette
A first position
B second position
C vapour channel
P flow path

The invention claimed is:

1. A reservoir assembly for a personal vaporizer device, such as an electronic smoking article, comprising:
   a housing which encloses a reservoir for storing a liquid to be vaporized, the housing and/or the reservoir defining a flow path for the liquid from the reservoir towards a vaporizer; and
   a mouthpiece provided in or on the housing and defining a channel for conveying vapour formed from the liquid to a user's mouth;
   wherein the mouthpiece is configured for movement between a first position and a second position, and wherein the flow path is closed or blocked when the mouthpiece is in the first position and wherein the flow path is open in the second position, wherein a part of the mouthpiece blocks the flow path in the first position, and wherein the reservoir surrounds a central cavity in the housing; and wherein the central cavity accommodates the mouthpiece.

2. The reservoir assembly according to claim 1, wherein the flow path comprises a flow port formed in a wall of the reservoir, and wherein the mouthpiece comprises a sealing portion which covers or blocks the flow port when the mouthpiece is in the first position.

3. The reservoir assembly according to claim 1, wherein the mouthpiece is configured to be substantially retracted into the housing in the first position.

4. The reservoir assembly according to claim 1, wherein the mouthpiece is configured to extend or project from the housing in the second position.

5. The reservoir assembly according to claim 1, wherein the mouthpiece comprises an elongate member having the channel extending longitudinally thereof, and wherein the mouthpiece is movable in the longitudinal direction between the first position and the second position.

6. The reservoir assembly according to claim 1, wherein the mouthpiece is resiliently biased towards the first position.

7. The reservoir assembly according to claim 1, wherein the mouthpiece is configured for translational or sliding movement between the first position and the second position.

8. The reservoir assembly according to claim 1, wherein the mouthpiece is configured for rotational movement between the first position and the second position.

9. The reservoir assembly according to claim 1, wherein the housing is configured to receive, at least partially, an aerosol generating means of the personal vaporizer device, wherein the mouthpiece is configured for movement from the first position to the second position when the aerosol generating means is inserted into or received in the housing, and wherein the mouthpiece is configured for movement from the second position to the first position when the aerosol generating means is removed or withdrawn from the housing.

10. A personal vaporizer device, especially an e-cigarette, comprising:

the reservoir assembly according to claim 1; and a vaporizer; and a power supply for powering the vaporizer to vaporize the liquid from the reservoir.

11. The personal vaporizer device according to claim 10, wherein the housing is configured to receive, at least partially, the vaporizer of the personal vaporizer device, and wherein the mouthpiece is configured for movement from the first position to the second position upon insertion of the vaporizer into the housing.

12. The personal vaporizer device according to claim 10, wherein the power supply is a battery unit and includes a casing configured for connection with the housing of the reservoir assembly, wherein the casing is configured for connection with the housing in a friction fit or in a threaded or a latched connection.

13. The reservoir assembly according to claim 6, wherein the mouthpiece is resiliently biased towards the first position by spring means.

* * * * *